United States Patent
Kim et al.

(10) Patent No.: US 7,385,689 B2
(45) Date of Patent: Jun. 10, 2008

(54) METHOD AND APPARATUS FOR INSPECTING SUBSTRATE PATTERN

(75) Inventors: Kye-Weon Kim, Suwon-si (KR); Chung-Sam Jun, Suwon-si (KR); Ki-Suk Chung, Seoul (KR); Sang-Mun Chon, Yongin-si (KR); Seong-Jin Kim, Yongin-si (KR); Byung-Sug Lee, Suwon-si (KR); Yu-Sin Yang, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 353 days.

(21) Appl. No.: 11/207,772

(22) Filed: Aug. 22, 2005

(65) Prior Publication Data
US 2006/0039598 A1    Feb. 23, 2006

(30) Foreign Application Priority Data
Aug. 23, 2004   (KR) ...................... 10-2004-0066203

(51) Int. Cl.
*G01N 21/00*    (2006.01)

(52) U.S. Cl. .................. 356/237.5; 356/71; 356/237.4; 356/239.3; 382/144; 382/149

(58) Field of Classification Search ............... 356/71, 356/237.4–237.5, 239.3; 382/144–149
See application file for complete search history.

(56) References Cited

U.S. PATENT DOCUMENTS

| 6,266,437 | B1 * | 7/2001 | Eichel et al. ............... 382/149 |
| 6,411,377 | B1 * | 6/2002 | Noguchi et al. .......... 356/237.4 |
| 6,836,560 | B2 * | 12/2004 | Emery ......................... 382/145 |
| 6,952,491 | B2 * | 10/2005 | Alumot et al. ........... 356/237.4 |
| 7,135,259 | B2 * | 11/2006 | Chen et al. ................. 356/957 |

FOREIGN PATENT DOCUMENTS

| JP | 10-281732 | 10/1998 |
| JP | 2001-330421 | 11/2001 |
| JP | 2002-261139 | 9/2002 |

* cited by examiner

*Primary Examiner*—Gregory J. Toatley, Jr.
*Assistant Examiner*—Iyabo S Alli
(74) *Attorney, Agent, or Firm*—Volentine & Whitt, PLLC

(57) ABSTRACT

A method of inspecting an inspection pattern using a statistical inference function is disclosed. The inference function is generated in relation to optical reference signal data and reference pattern characteristic data for a plurality of reference patterns formed by a unit process of interest on reference substrates.

35 Claims, 6 Drawing Sheets

METHOD AND APPARATUS FOR INSPECTING SUBSTRATE PATTERN

BACKGROUND OF THE INVENTION

1. Field of the Invention

The present invention relates to an apparatus adapted to inspect a pattern on a substrate and a related method. More particularly, the invention relates to a method and apparatus adapted to inspect a pattern characteristic using a statistical inference function using a light signal corresponding to the pattern characteristic.

This application claims the benefit of Korean Patent Application No. 2004-66203 filed on Aug. 23, 2004, the subject matter of which is hereby incorporated by reference in its entirety.

2. Description of the Related Art

As semiconductor devices have become more highly integrated and operating speeds have increased, design rules have changed. In general, a contact area and other critical dimensions defining the layout of contemporary semiconductor devices have gradually been reduced. These even smaller dimensions are increasingly intolerant to design and manufacturing errors. Yet, such ever smaller defects are harder and harder to identify during quality assurance processes. For example, common processing defects include voids formed in an insulation interlayer and a bridge defect formed on the contact plug of a stacked capacitor structure. As the overall dimensions of these individual components have shrunk over time, the associated processing defects have become ever more small and difficult to locate.

Most processing defects are caused by a pattern defect. Hence, each thin layer formed by a unit process step during the manufacture of a semiconductor device must be inspected for the presence of pattern defects. For example, the thickness of a thin layer formed on a substrate must be inspected following a deposition process. The thickness and/or width of a substrate pattern must similarly be inspected following a photolithography process. Where an inspected thickness or width is determined to be outside the allowed error tolerance, the process conditions associated with the unit process are often changed to prevent the subsequent formation of additional processing defects.

A scanning electron microscope (SEM) measurement or an optical measurement is widely utilized in pattern inspection processes.

A conventional SEM measurement technique typically involves direct examination of a substrate portion (hereafter the "specimen") including the pattern to be inspected. To do this, an electron beam is projected onto a cross sectional surface of the specimen, and secondary electrons are discharged from the specimen. The discharged secondary electrons are detected by the SEM, and the SEM provides a corresponding two dimensional image of the specimen, or the inspection pattern. This image is often referred to as a vertical profile of the inspection pattern. The physical properties of the inspection pattern such as a thickness, a width and a height are directly measured from the vertical profile of the inspection pattern. From the physical properties determined by the SEM measurement, a direct determination may be made as to whether or not the measured physical properties meet design specifications (e.g., fall within error tolerances).

Unfortunately, the SEM measurement requires a vacuum state and a lengthy examination period in order to provide satisfactory inspection results. The slow rate of inspection provided by SEM measurements is particularly disadvantageous in the context of modern manufacturing facilities which require highly efficient processes in order to ensure commercially viable productivity.

A conventional optical measurement technique typically involves periodically irradiating a surface portion of a substrate containing the desired inspection pattern, and detecting an optical signal reflected from the inspection pattern using an optical detector. The reflection optical signal is thereafter analyzed by the complex combination of a matrix function and an electromagnetic function to determine the physical properties of the inspection pattern and to estimate whether or not the obtained physical properties are within the allowable tolerance limits.

The conventional optical measurement technique provides fairly accurate results where the inspection pattern is formed with a relatively simple, two-dimensional matrix shape. However, the conventional optical measurement technique has a great difficulty analyzing the large number of reflected optical signals generated by more complicated inspection patterns. Indeed, such analysis typically requires the use of a costly computer server to process a large number of complex, reflected optical signals.

Thus, the two most common techniques used to detect pattern defects require an examination of the physical properties of the inspection pattern. Yet, an accurate measurement of the physical properties of an inspection pattern is not necessarily required for the detection of pattern defects, and further reliance on the examination of physical properties will only become ever more fruitless as pattern designs are defined in smaller and smaller dimensions. For these reasons, ongoing research continues into the problems associated with pattern defect inspections and the proper formation of patterns on semiconductor devices.

For example, Japanese Patent Laid-Open Publication No. 2002-261139 discloses a method of forming a pattern with optimal thickness or width by optimally varying the processing conditions during a unit process in accordance with variations in the amount of light reflected from the surface of an inspection pattern.

Unfortunately, this disclosure has a problem in that the optimal reflection light and the optimal pattern have no unique correspondence with each other, since an accurate statistical analysis correlating the reflection light and physical properties of the inspection pattern are not usually known.

Additionally, Japanese Patent Laid-Open Publication No. 2001-330421 discloses a method of inspecting a pattern using a surface ratio for the pattern with respect to the underlying substrate. That is, the surface ratio is obtained by relating a detection pulse derived from a light reflected from the surface of the inspection pattern and an output pulse derived from a source light irradiating the substrate. Yet, unfortunately, this disclosure has limited utility to only those inspection patterns having clear periodic features repeated across the substrate since the surface ratio of the inspection pattern is obtained from the ratio of the inspection pulse with respect to the output pulse. Accordingly, the inspection method proposed in this Japanese laid-open patent document cannot be applied to inspection patterns lacking such periodic features.

These disclosures are but two examples of the many inadequate attempts previously made to develop an improved method of inspecting for defects in an inspection pattern without the requirement of accurately measuring the physical properties of the inspection pattern.

SUMMARY OF THE INVENTION

Embodiments of the present invention provide a method of inspecting an inspection pattern on a substrate capable of inspecting pattern defects in the inspection pattern without the requirement for accurately measuring the physical properties of the inspection pattern. Embodiments of the invention also provide an apparatus for performing the this method.

For example, in one embodiment, the invention provides a method of inspecting an inspection pattern formed on an inspection substrate by a unit process, comprising; generating a statistical inference function corresponding to optical reference signal data and reference pattern characteristic data associated with a plurality of reference patterns formed on reference substrates by the unit process, obtaining optical reference signal data from inspection light reflected from the inspection pattern, calculating inspection pattern characteristic data from the optical reference signal data and the statistical inference function, and determining whether or not the calculated inspection pattern characteristic data falls within an allowable error tolerance range.

In a related aspect, generating the statistical inference function comprises; forming optical signal groups, each of the optical signal groups comprising optical reference signal data and being arranged in accordance with the wavelength of the inspection light, forming a pattern characteristic group comprising reference pattern characteristic data, repeatedly performing a correlation analysis between the optical reference signal data in each optical signal group and reference pattern characteristic data to thereby obtain a correlation factor corresponding to each of the optical signal groups, and performing a regression analysis between optical reference signal data in a reliable signal group and reference pattern characteristic data to thereby generate a regression line associated with the statistical inference function, wherein the reliable signal group corresponds to an allowable correlation factor and a reliable wavelength for the inspection light.

The inspection light may comprise light having ultraviolet or deep ultraviolet wavelengths, and the optical reference signal data may comprise an intensity value associated with the reflected inspection light.

Further, the inspection light may comprise polarized light, and the optical reference signal data may comprise a tangent of a ratio between a vertical component and a horizontal component of the polarized light, or a cosine of a phase difference between the vertical component and the horizontal component of the polarized light. In relation to this aspect, the correlation factor includes a Pearson's correlation coefficient.

The reference pattern characteristic data may be derived from measurements made with a scanning electron microscope (SEM). Further, the reference pattern characteristic data may correspond to the width or thickness of a reference pattern and the regression line may comprise a simple regression line using the width or thickness of the reference pattern as a predictor and the optical reference signal data as a criterion.

Alternatively, the reference pattern characteristic data may comprise the width and thickness of the reference pattern, and the regression line may thus comprise a multiple regression line using the width and thickness of the reference pattern as a predictor and the optical reference signal data as a criterion.

In another embodiment, the foregoing method further comprise; adding current optical reference signal data to the reference pattern optical signal data in relation to the wavelength of the inspection light to thereby modify the corresponding optical signal group, adding the actual inspection pattern characteristic data to the reference pattern characteristic data to thereby modify the corresponding pattern characteristic group; and thereafter generating a modified statistical inference function from the modified optical signal group and the modified pattern characteristic group.

In yet another embodiment, the foregoing method further comprises; deriving actual inspection pattern characteristic data to thereby form a plurality of actual inspection pattern characteristic data, adding current optical reference signal data to the reference pattern optical signal data in relation to the wavelength of the inspection light to thereby modify the optical signal group, adding the actual inspection pattern characteristic data to the reference pattern characteristic data to thereby modify the pattern characteristic group, and generating a modified statistical inference function in relation to the modified optical signal group and the modified pattern characteristic group.

In still another embodiment, the invention provides an apparatus for inspecting an inspection pattern formed on an inspection substrate by a unit process, comprising; a stage adapted to secure the inspection substrate, an irradiating member adapted to irradiate the inspection substrate with an inspection light, a detecting member adapted to detect inspection light reflected from the inspection substrate and generate optical reference signal data corresponding to the reflected inspection light, and an operating member adapted to determine whether a pattern defect is present in the inspection pattern by calculating inspection pattern characteristic data using a statistical inference function, wherein the statistical inference function corresponds to a relationship between the optical reference signal data and reference pattern characteristic data.

The reference pattern characteristic data may be derived from a plurality of reference patterns formed on reference substrates by the unit process.

In a related aspect, the stage may comprise a support unit adapted to support the inspection substrate and a drive unit adapted to move the support unit.

In another related aspect, the irradiating member may comprise; a light source adapted to generating the inspection light, and a beam splitter adapted to transforming the inspection light into a slit light. The detecting member may comprise; a detection lens adapted to detect the reflected inspection light, and a data generation unit adapted to generate the optical reference signal data from the reflected inspection light.

In yet another related aspect the light source may comprise a krypton fluoride (KrF) excimer laser, an argon fluoride (ArF) excimer laser, a fluorine (F2) excimer laser or an argon (Ar) excimer laser, and/or the inspection light may comprise light having an ultraviolet or deep ultraviolet (DUV) wavelength.

The data generation unit may comprise a charge coupled device (CCD) adapted to detect intensity of the reflected inspection light, such that the optical reference signal data corresponds to the detected intensity of the reflected inspection light.

In yet another related aspect, the irradiating member may comprise a light source adapted to generate the inspection light and a polarizer for transforming the inspection light into a polarized light, and the detecting member may comprise a detection lens adapted to detect polarized light reflected from the inspection substrate, a resolution unit adapted to resolve the reflected polarized light into vertical and horizontal components, and a data generation unit adapted to generate the optical reference signal data from the vertical and horizontal components.

In still another related aspect, the data generation unit may be adapted calculate an intensity ratio ($\Psi$) between the vertical and horizontal components of the reflected polarized light, and the optical reference signal data corresponds to a tangent of the intensity ratio (tan $\Psi$).

Alternatively or additionally, the data generation unit may be adapted to calculate a phase difference ($\Delta$) between the vertical and horizontal components of the reflected polarized light, and the optical reference signal data corresponds to a cosine of the phase difference (cos $\Delta$).

In another embodiment, the foregoing apparatus may further comprises; a storage member storing a plurality of optical signal groups in accordance with a wavelength of a reference light supplied onto the reference substrates in a first data file, and storing a pattern characteristic group in a second data file, wherein each optical signal group comprises optical reference signal data and the pattern characteristic group comprises reference pattern characteristic data.

In a related aspect, the function generation unit may comprise a regression analyzer adapted to perform a regression analysis between optical reference signal data and the reference pattern characteristic data transmitted to the function generation unit from the first and second data files, respectively. In yet another related aspect, the function generation unit may further comprise; a correlation analyzer adapted to measure a correlation factor between the optical reference signal data in a selected optical signal group and the wavelength of the reference light corresponding to the selected optical signal group, and wherein the regression analyzer performs the regression analysis between the optical reference signal data in a reliable signal group having an allowable correlation factor and the reference pattern characteristic data.

BRIEF DESCRIPTION OF THE DRAWINGS

Several exemplary embodiments of the invention are described hereafter in some additional detail with reference to the drawings in which.

DESCRIPTION OF THE EMBODIMENTS

As will be set forth in some additional detail below, the inspection pattern characteristic data provided by the invention is calculated from a statistical inference function and related optical inspection signal data. Based on this data, a determination is made as to whether or not a related inspection pattern has been formed by a unit process of interest with an allowable error tolerance range. By use of an embodiment implemented according to the dictates of the invention, the cost and time associated with the inspection process are remarkably reduced.

In additional embodiments of the invention, the optical reference signal data and the inspection pattern characteristic data actually measured during the inspection process are accumulated in order to established optical signal group(s) and pattern characteristic group(s), so that confidence in the inference function is improved over time. As a result, although an inspection process adapted to examine the inspection pattern characteristics, per se, is not actually performed, pattern defects may nonetheless be accurately determined by use of the inference function. Additionally, because optical reference signal data derived during repeated executions of the inspection process is accumulated to good statistical use, an expensive apparatus required to analyze the optical signal data is not needed. The inspection efficiency is remarkably improved since the inspection process mainly depends on a statistical treatment provided by an associated computer system, so throughput of the inspection process is remarkably increased.

Figure 1:
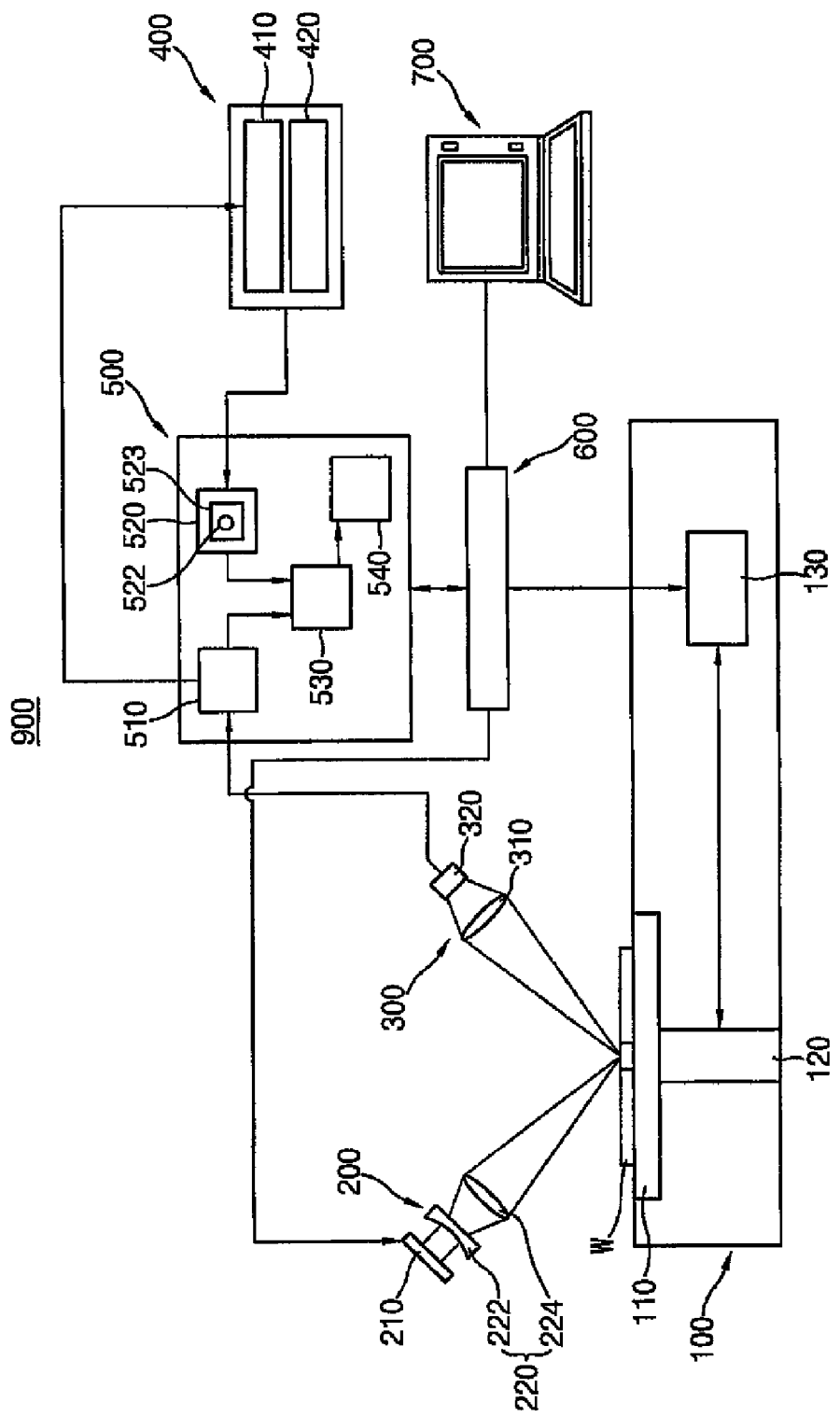
FIG. 1 is schematic view illustrating an apparatus for inspecting an inspection pattern on a substrate according to an exemplary embodiment of the present invention.

FIG. 1 is schematic view illustrating an apparatus for inspecting an inspection pattern on a substrate according to one embodiment of the invention.

Referring to FIG. 1, an apparatus 900 adapted to inspect an inspection pattern and including a stage 100 supporting a substrate W to be inspected, an irradiating member 200 adapted to irradiate the substrate with an inspection light, a detecting member 300 adapted to generate a optical inspection signal data related to the inspection pattern, a data storage member 400 adapted to store optical reference signal data related to reference pattern characteristic data, an operating member 500 adapted to detecting a pattern defect in the inspection pattern, and a controller 600 adapted to systematically control stage 100, irradiating member 200, detecting member 300, data storage member 400, and operating member 500.

Inspection substrate W will typically comprises a silicon wafer conventionally used in the manufacture of semiconductor devices. The inspection pattern formed on inspection substrate W may be variously formed according to one of any number of conventional techniques, such as forming a photoresist pattern using a photolithography process and a mask pattern prior to an etching process.

In one embodiment, stage 100 comprises a support unit 110 supporting substrate W on which the inspection pattern is formed. Stage 100 also includes a drive unit 120 adapted to drive support unit 110 and thereby adjust the position of substrate W. The top surface of support unit 110 will normally be flat so as to securely support inspection substrate W in a horizontal position. Drive unit 120 is typically connected to a bottom (or side) surface of support unit 110 in such a manner that support unit 110 may be precisely positioned. One example of a possible drive unit 120 comprises a three-dimensional transfer mechanism.

Stage 100 is also associated in one embodiment with a driver 130 electrically connected to drive unit 120. Driver 130 is preferably controlled by controller 600. Accordingly, controller 600 may adjust the position of inspection substrate W through driver 130 and driving unit 120 in accordance with various processing conditions.

In one exemplary embodiment, irradiating member 200 comprises a light source 210 adapted to generate the inspection light and a beam splitter 220 receiving the inspection light and adapted to transform the inspection light into a slit light. In one embodiment, light source 210 comprises a laser, such as a krypton fluoride (KrF) excimer laser, an argon fluoride (ArF) excimer laser, a fluorine (F2) excimer laser, or an argon (Ar) excimer laser. However, the inspection light generated by light source 210 may be ultraviolet or deep ultraviolet (DUV), as well as any wavelength conventionally generated by the above laser types. Beam splitter 220 typically comprises a lens assembly having a pair of concave and convex lenses 222 and 224. Use of beam splitter 220 improves the measurement rate of physical properties associated with the inspection pattern.

In one embodiment, detecting member 300 comprises a detection lens 310 adapted to detect the light reflected from inspection substrate W. Detecting member 300 also comprises a data generation unit 320 adapted to generate the optical inspection signal data from the reflected light passing through detection lens 310. Detection lens 310 comprises an objective lens having a predetermined aperture to condense the reflected light. Thereafter, data generation unit 320 manipulates the reflected light passing through the detection lens 310 to generate the optical inspection signal data.

In one related embodiment, a charge coupled device (CCD) sensor may be used to form data generation unit 320. Where used in this capacity, the CCD sensor transforms free electrons received as part of the reflected inspection light into a corresponding electrical signal. The optical properties of the reflected inspection light, such as intensity and wavelength, will vary in accordance with physical properties of the inspection pattern on inspection substrate W. In particular, the thickness or width of the inspection pattern has a large effect on the optical properties of the reflected inspection light. The electrical signal generated by the CCD sensor forming data generation unit 320 will normally be proportional to the intensity of the reflected inspection light, so that the CCD sensor is able to uniquely determine and indicate an intensity value. Thus, in the working examples, a CCD sensor derived intensity value for the reflected inspection light forms an excellent basis for the optical inspection signal data.

Thus, in the foregoing exemplary embodiments, conventional optical system components may be used to form irradiating member 200 and detecting member 300. However, irradiating member 200 and detecting member 300 might also be constructed using a spectroscopic ellipsometer (SE) adapted to non-destructively measure the thickness of an inspection pattern. The SE may be used to provide a polarized inspection light which is reflected off the surface of an inspection substrate and then resolved into vertical and horizontal components. An intensity ratio between the vertical component and the horizontal component, as well as a phase difference between the vertical and horizontal components may be used to form the optical inspection signal data.

Figure 2:
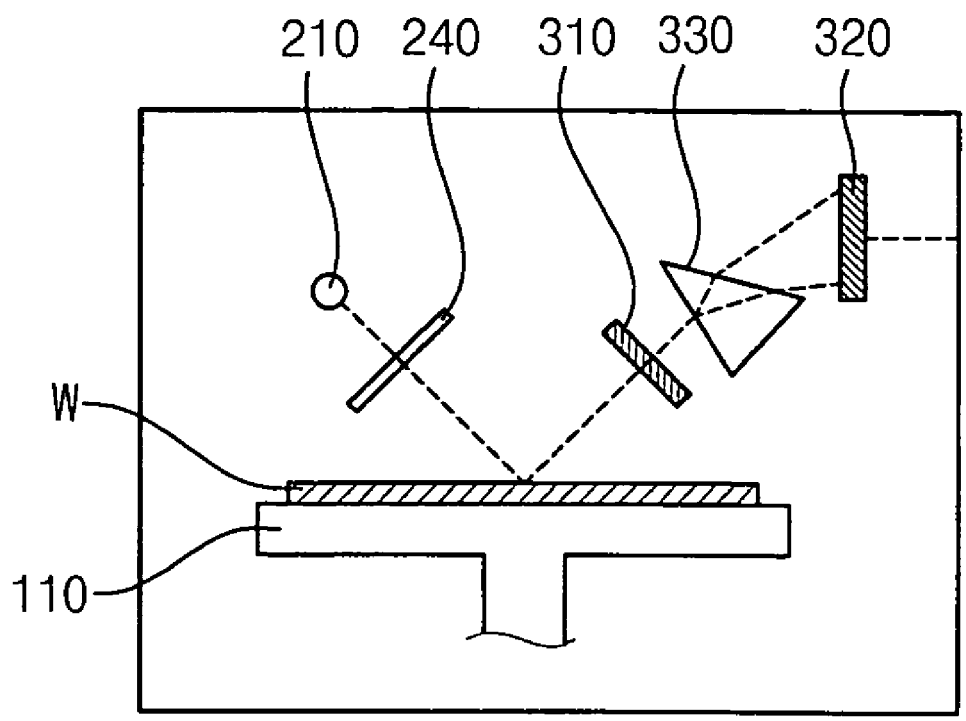
FIG. 2 is schematic view illustrating an apparatus for inspecting an inspection pattern when the spectroscopic ellipsometer (SE) is used for measuring the pattern properties.

FIG. 2 is schematic diagram further illustrating an apparatus adapted to inspect an inspection pattern using a SE.

Referring to FIG. 2, irradiating member 200 comprises light source 210 adapted to generate an inspection light and a polarizer 240 adapted to transform the inspection light into a polarized light. Detecting member 300 comprises detection lens 310 adapted to detect polarized light reflected from the surface of inspection substrate W. A resolution unit 330 adapted to resolve the reflected polarized light into vertical and horizontal components is also provided. Detecting member 300 also comprises data generation unit 320 adapted to generate an intensity ratio and a phase difference between the vertical and horizontal components of the reflected polarized light.

Within this particular embodiment, the inspection light is transformed into polarized light by passing through polarizer 240, such that an inspection light polarized along one or more predetermined axes is irradiated onto the surface of inspection substrate W. A portion of this polarized inspection light is reflected from the surface.

In one related present embodiment, resolution unit 330 comprises a prism. The reflected polarized light is resolved into vertical and horizontal components by the prism. Data generation unit 320 then calculates the intensity ratio ($\Psi$) and the phase difference ($\Delta$) between the vertical and horizontal components of the reflected polarized light based on a conventional SE theory well known to those skilled in the art. In such a case, a tangent of the intensity ratio (tan $\Psi$) or a cosine of the phase difference (cos $\Delta$) may be used as the basis for the formation of the optical inspection signal data.

Referring now again to FIG. 1, storage member 400 stores an optical reference signal data and/or reference pattern characteristic data that may be statistically manipulated to generate an inference function correlating the optical inspection signal data and the pattern characteristic data. In combination, the inference function and the optical inspection signal data may thus be used to generate inspection pattern characteristic data. This inspection pattern characteristic data may subsequently be used to determine the presence of a pattern defect in the inspection pattern. Accordingly, the optical reference signal data and the reference pattern characteristic data serve as reference or comparative data during the inspection method of the present invention. Thus, these values are measured or derived during the inspection method regardless of particulars of the method.

In anticipation of the inspection process, reference substrates are carefully prepared to accurately generate the foregoing reference data. The reference substrates then undergo the same inspection process as is intended for an inspection substrate. The process of preparing and inspecting references substrates involves selecting a particular unit process of interest, then processing the reference substrate across a range of possible process conditions associated with the unit process, and then inspecting the resulting layer, pattern, etc., to be formed by the unit process.

In the examples that follow, the width of a photoresist pattern is inspected. This is a common necessity as inspection patterns related to photoresist patterns used during photolithography are a typical inspection requirement. However, this is just a selected example. The present invention is not limited to only the foregoing exemplary inspection system, and it isn't limited to only the inspection of line widths in a photoresist pattern.

An amount of light to which a photoresist layer is exposed and a focal distance of the exposing system have a great effect on the resulting width of a photoresist pattern. Hence, these two process conditions are critical to the accurate formation of line widths in the photoresist pattern. The width of the photoresist pattern digresses from optimal in direct relation to digressions of the light amount from an optimal light amount and with digressions of the focal distance from an optimal focal distance. Table 1 shows a width range of variations in such processing conditions.

TABLE 1

|        | B − 3a  | B − 2a   | B − a    | B        | B + a    | B + 2a   | B + 3a |
|--------|---------|----------|----------|----------|----------|----------|--------|
| A + 2d | Defect  | Defect   | Defect   | Defect   | Defect   | Defect   | Defect |
| A + d  | Defect  | Marginal | Marginal | Marginal | Marginal | Marginal | Defect |
| A      | Defect  | Marginal | Marginal | Optimal  | Marginal | Marginal | Defect |
| A − d  | Defect  | Marginal | Marginal | Marginal | Marginal | Marginal | Defect |
| A − 2d | Defect  | Defect   | Defect   | Defect   | Defect   | Defect   | Defect |

In Table 1, the letter "A" indicates an optimal focal distance and the letter "B" indicates an optimal light amount. The "optimal' cell in Table 1 indicates optimal processing conditions that result in an optimal width of the photoresist pattern. "Marginal" cells in Table 1 indicate a range of processing errors related to the light amount and/or the focal distance that are non-optimal, but that result in photoresist pattern widths that nonetheless fall within established tolerances. "Defect" cells in Table 1 indicate departures from the optimal processing conditions that result in photoresist pattern widths outside of the established tolerances. These widths result in a pattern defect associated with the photolithography process. Of note, reference substrates containing photoresist patterns characterized by line widths resulting from process conditions corresponding to the marginal cells and defect cells are prepared, as well as one or more reference substrates containing photoresist patterns characterized by line width(s) resulting from process conditions corresponding to the optimal cell in Table 1.

Thereafter, using irradiating member 200, a reference light is irradiated onto each of the reference substrates on which a particular "reference pattern" (e.g., a photoresist pattern) has been formed. Reflected reference light from the surface of each reference substrate is then detected by detecting member 300 to thereby generate a corresponding optical reference signal data indicating corresponding pattern characteristic data (e.g., the width of the photoresist pattern).

The foregoing is just one presently preferred technique to obtain pattern characteristic data and indicating optical reference signal data. Other techniques may be used to obtain similar results. For example, the pattern characteristic data may be obtained via direct measurement of pattern widths using a conventional measuring apparatus such as a scanning electron microscope (SEM).

In one set of experiments run in relation to an embodiment of the present embodiment, twenty-four reference substrates were prepared, and reference pattern widths and optical reference signal data were measured for each reference pattern on the reference substrate. Each of the twenty-four reference substrates was prepared under a different set of processing conditions representing possible variations from an optimal set of processing conditions. A corresponding plurality of the reference widths and optical reference data signals were also obtained. These are recorded in Table 2.

TABLE 2

| Wave length | 400.42 | 401.03 | 401.63 | ... | 435 | 435.5 | 436 | ... | 595.65 | 597.62 | 599.61 | width |
|---|---|---|---|---|---|---|---|---|---|---|---|---|
| S01 | 1.94931 | 1.90818 | 1.86599 | ... | 0.707 | 0.694 | 0.682 | ... | 0.89779 | 0.91077 | 0.92375 | 177.7 |
| S02 | 1.96401 | 1.92338 | 1.88140 | ... | 0.717 | 0.705 | 0.693 | ... | 0.89448 | 0.90773 | 0.92105 | 177.2 |
| S03 | 2.01758 | 1.97892 | 1.93744 | ... | 0.753 | 0.740 | 0.728 | ... | 0.86867 | 0.88226 | 0.89600 | 178.5 |
| S04 | 2.09997 | 2.06783 | 2.03229 | ... | 0.808 | 0.793 | 0.780 | ... | 0.82892 | 0.84277 | 0.85665 | 179.6 |
| S05 | 2.15227 | 2.13796 | 2.11586 | ... | 0.877 | 0.861 | 0.846 | ... | 0.80582 | 0.81974 | 0.83359 | 184.2 |
| S06 | 1.94919 | 1.90506 | 1.86057 | ... | 0.711 | 0.699 | 0.687 | ... | 0.88434 | 0.89844 | 0.91268 | 172.8 |
| S07 | 1.97502 | 1.93098 | 1.88472 | ... | 0.731 | 0.718 | 0.705 | ... | 0.86949 | 0.88391 | 0.89838 | 176.5 |
| S08 | 1.94716 | 1.90119 | 1.85465 | ... | 0.726 | 0.713 | 0.701 | ... | 0.86530 | 0.87965 | 0.89380 | 177.8 |
| S09 | 2.07599 | 2.03083 | 1.98192 | ... | 0.779 | 0.765 | 0.751 | ... | 0.83219 | 0.84682 | 0.86143 | 178.9 |
| S10 | 2.11331 | 2.07816 | 2.03986 | ... | 0.812 | 0.796 | 0.782 | ... | 0.81741 | 0.83172 | 0.84610 | 181.8 |
| S11 | 1.95329 | 1.90793 | 1.86040 | ... | 0.718 | 0.705 | 0.693 | ... | 0.87827 | 0.89295 | 0.90763 | 175.6 |
| S12 | 1.86498 | 1.81885 | 1.77299 | ... | 0.688 | 0.676 | 0.664 | ... | 0.88849 | 0.90318 | 0.91785 | 175.6 |
| S13 | 1.89333 | 1.84527 | 1.79716 | ... | 0.709 | 0.696 | 0.684 | ... | 0.87405 | 0.88874 | 0.90330 | 177.0 |
| S14 | 1.97527 | 1.91965 | 1.86592 | ... | 0.733 | 0.719 | 0.707 | ... | 0.86094 | 0.87562 | 0.89047 | 178.3 |
| S15 | 2.10883 | 2.06627 | 2.01963 | ... | 0.794 | 0.779 | 0.765 | ... | 0.82427 | 0.83901 | 0.85367 | 179.5 |
| S16 | 2.05754 | 2.01196 | 1.96549 | ... | 0.758 | 0.744 | 0.731 | ... | 0.86520 | 0.88012 | 0.89499 | 176.3 |
| S17 | 2.04638 | 1.99899 | 1.95074 | ... | 0.755 | 0.741 | 0.728 | ... | 0.86817 | 0.88307 | 0.89796 | 177.5 |
| S18 | 2.07113 | 2.02527 | 1.97759 | ... | 0.773 | 0.758 | 0.745 | ... | 0.84204 | 0.85687 | 0.87178 | 179.3 |
| S19 | 2.09098 | 2.04657 | 2.00116 | ... | 0.782 | 0.768 | 0.754 | ... | 0.84385 | 0.85877 | 0.87358 | 181.5 |
| S20 | 2.19782 | 2.16822 | 2.13447 | ... | 0.862 | 0.845 | 0.829 | ... | 0.78926 | 0.80420 | 0.81897 | 181.8 |
| S21 | 2.09498 | 2.05159 | 2.00442 | ... | 0.781 | 0.767 | 0.753 | ... | 0.85361 | 0.86852 | 0.88346 | 179.8 |
| S22 | 2.15765 | 2.12315 | 2.08446 | ... | 0.830 | 0.814 | 0.799 | ... | 0.82325 | 0.83799 | 0.85268 | 182.1 |
| S23 | 2.18184 | 2.15158 | 2.11610 | ... | 0.849 | 0.833 | 0.818 | ... | 0.81670 | 0.83154 | 0.84640 | 183.2 |
| S24 | 2.20080 | 2.17854 | 2.15120 | ... | 0.885 | 0.867 | 0.850 | ... | 0.78154 | 0.79651 | 0.81134 | 183.4 |
| Correlation coefficient | 0.854 | 0.865 | 0.871 | ... | 0.903 | 0.904 | 0.908 | ... | 0.859 | 0.861 | 0.864 | |

Values S01 through S24 recorded in the first column of Table 2 denote individual reference substrates. The last column in Table 2 records the measured width of the photoresist pattern for each reference substrate. A SEM was used to measure the pattern widths which are expressed in micrometer (μm) units. The first row of Table 2 records the wavelength of the reference light used to irradiate the reference substrates. Wavelengths are expressed in nanometer (nm) units. The last row of Table 2 records a correlation coefficient numerically indicating the degree of the correlation between each measured pattern width for a particular wavelength of the reference light. Corresponding optical reference signal data may be derived from Table 2 by finding the tangent of the intensity ratio (tan Ψ) between the vertical and horizontal components of the polarized reflection light reflected from each reference substrate.

Optical reference signal data shown along each column of Table 2 forms an optical signal group. Table 2 thus expresses a plurality of the optical signal groups correspondently to particular wavelengths of reference light. In other words, each optical signal group corresponds to a particular wavelength of reference light and includes a plurality of the optical reference data optical signals generated by the reference light when it is used to irradiate the reference substrates. Such pluralities of the optical signal groups, including the optical reference signal data, may be stored in a first data file 410 in data storage member 400. Continuing with the working example, a plurality of the measured photoresist pattern widths forming a width group corresponding to the various reference patterns may be stored in a second data file 420.

Operating member 500 is adapted to statistically operate on the optical reference signal data and the measured pattern width(s) to thereby generate an inference function correlating these two metrics. In one exemplary embodiment set forth in some additional detail hereafter, when the optical inspection signal data is set into the inference function, the inspection pattern characteristic data may be obtained with a predetermined confidence level.

Operating member 500 comprises a function generation unit 520 adapted to generate an inference function correlating optical reference signal data and measured pattern widths. In one embodiment, function generation unit 520 may include a regression analyzer 523 performing a linear regression analysis. The regression analyzer may further include a correlation analyzer 522 measuring a correlation factor between the optical reference signal data in an optical signal group and the wavelength of the reference light corresponding to the optical signal group.

Correlation analysis is a kind of statistical analysis measuring the degree of correlation between continuous and independent variables so that the degree of correlation between the two variables, which is a qualitative amount, may be quantified and numerically expressed. A simple correlation analysis, such as correlation analysis between two continuous and independent variables, may be generally expressed as a Pearson's correlation coefficient (r). A Pearson's correlation coefficient (r) is an arbitrary real number in a range from −1 to +1. When the absolute value of a Pearson's correlation coefficient (r) reaches +1, the two continuous and independent variables are proportional to each other. When the absolute value of a Pearson's correlation coefficient (r) reaches zero, the two continuous and independent variables are not at all proportional to each other and are not correlated one to another.

A Pearson's correlation coefficient (r) may be expressed according to the following equation (1).

$$r = \frac{\sum_{i=1}^{n}(X_i - \overline{X})(Y_i - \overline{Y})}{(n-1)S_X S_Y} \quad (1)$$

In equation (1), "n" denotes a number of samples (24 in the working example), and "X" and "Y" are two continuous and independent variables denoting the optical reference signal data and pattern width, respectively, and $S_x$ and $S_y$ denote a standard deviation for X and Y, respectively.

The optical reference signal data are transmitted to correlation analyzer 522 from first data file 410 via a conventional data link. The reference pattern characteristic data is similarly transmitted to correlation analyzer 522 from second data file 420. The optical reference signal data and the reference pattern characteristic data are manipulated in correlation analyzer 522 using, for example, the formula shown in equation (1) to thereby generate correlation coefficient "r." The manipulation of optical reference signal data and reference pattern characteristic data is repeated by correlation analyzer 522 for each optical signal group in order to generate a plurality of the correlation coefficients uniquely corresponding to each optical signal group. Exemplary correlation coefficients are shown in the last row of Table 2 for respective optical signal groups in relation to the various wavelengths of the reference light.

Function generation unit 520 selects an allowable correlation coefficient from among the plurality of calculated correlation coefficients in relation to an optical signal group corresponding to the allowable correlation coefficient. Such selection forms a so-called reliable signal group. A statistical regression analysis is then performed between the optical reference signal data in the reliable signal group and the reference pattern characteristic data using function generation unit 520 to thereby generate a corresponding inference function for the optical reference signal data and reference pattern characteristic data. The wavelength of the reference light corresponding to the reliable signal group is referred to as a reliable wavelength.

For example, using the results shown in Table 2, if an allowable correlation coefficient is defined to be no less than about 0.9, the reliable signal group includes an optical signal group having a wavelength from about 435 nm to about 436 nm. In other words, the reliable wavelength of the reference light extends across a range of about 435 nm to about 436 nm when the allowable correlation coefficient is defined to be no less than about 0.9. The reliable signal group has a relatively strong positive correlation between the optical reference signal data and the reference pattern characteristic data, as compared with the other optical signal group, and thus the optical reference signal data in the reliable signal group are inferred to be strongly proportional to the corresponding pattern width. That is, when a reference light having a reliable wavelength is used to irradiate the surface of the reference substrates, there is a high probability that an increase of the optical reference signal data will indicate an increase in pattern width.

Figure 3:
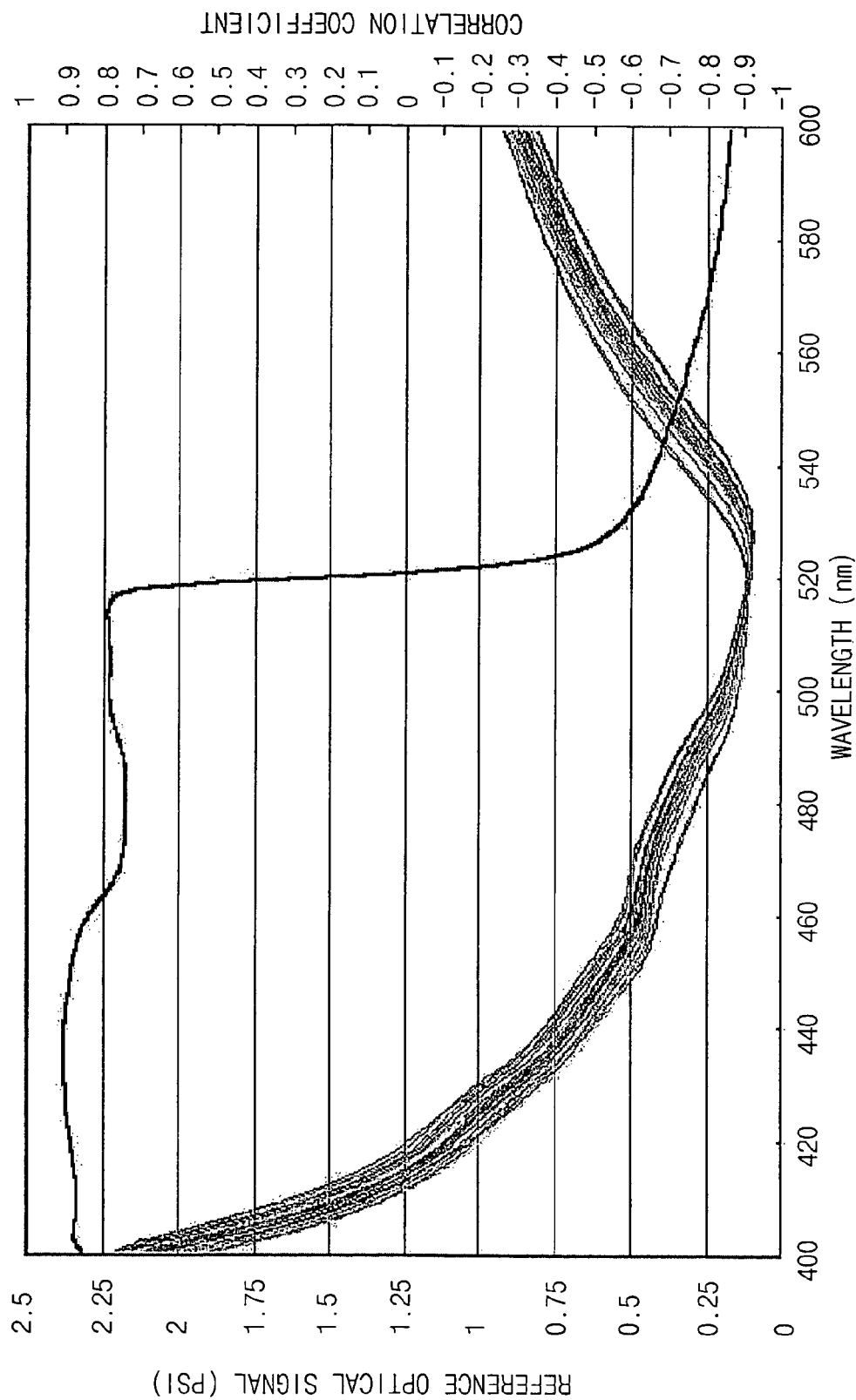
FIG. 3 is a graph of a continuous function showing a relationship between the reference optical signal data and the reference pattern characteristic data based on the discrete data in Table 2.
Figure 4:
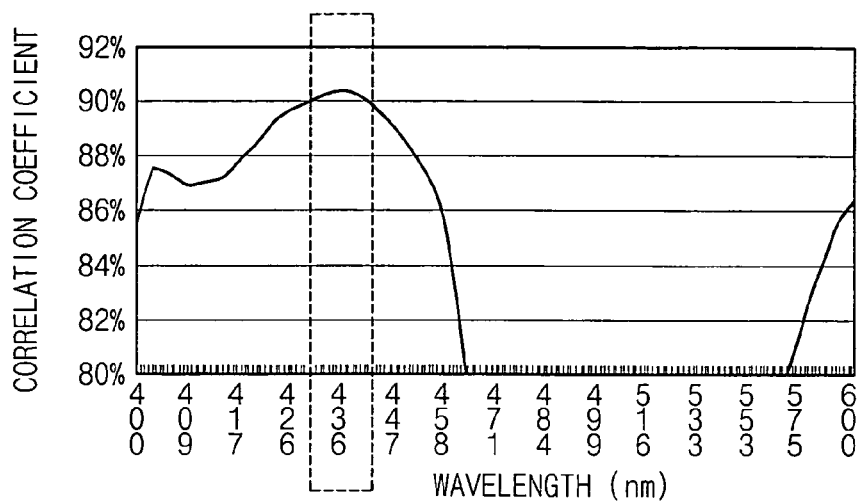
FIG. 4 is a graph of continuous function showing a relationship between the wavelength of the reference light and the correlation coefficients based on the discrete data in Table 2.

FIG. 3 is a graph of a continuous function showing the relationship between optical reference signal data and reference pattern characteristic data based on the discrete data contained in Table 2. FIG. 4 is a graph of continuous function showing the relationship between the wavelength of the reference light and the correlation coefficients derived from the discrete data contained in Table 2.

Referring to FIGS. 3 and 4, the correlation coefficient between the optical reference signal data and reference pattern width approaches 1 when the wavelength of the reference light is in a range from about 420 nm to about 440 nm. In particular, the correlation coefficient is the most close to 1 when the wavelength of the reference light is about 436 nm.

An allowable correlation coefficient may be defined in view of particular processing conditions for unit process of interest and the corresponding inspection conditions. The optical signal group corresponding to the allowable correlation coefficient is selected as the reliable signal group. As a result, only the optical reference signal data in the reliable signal group is used for the regression analysis, so that the confidence level associated with the regression line may be increased. In addition, the inspection light used to irradiate the subject inspection substrate is set to have the reliable wavelength, thereby allowing the confidence level associated with the inspection pattern characteristic data to be increased.

When a photoresist pattern width is inspected during in a photolithography process, according to one exemplary embodiment of the invention, the inspection results are sufficiently satisfactory if the allowable correlation coefficient is not less than about 0.8. A range for the allowable correlation coefficient may be varied in view of the process conditions associated with the unit process of interest and related inspection accuracy thresholds and inspection conditions.

Function generator unit 520 conducts the regression analysis between the optical reference signal data in the reliable signal group and the reference pattern characteristic data. In one embodiment of the invention, the optical reference signal data corresponding to the wavelength of about 435 nm and the measured pattern width shown in Table 2 are exemplarily provided for the regression analysis. Although the above exemplary embodiment selects the optical reference signal data corresponding to a wavelength of about 435 nm for the regression analysis, the regression analysis may be performed with any optical reference signal data, but only if the optical reference signal data is included in the reliable signal group, thereby generating the inference function with respect to the optical reference signal data in the reliable signal group.

While the foregoing correlation analysis provides a degree of the correlation between independent and continuous variables, the regression analysis provides a functional relation between the correlated variables. According to the regression analysis, a proper mathematical model is selected and inferred at a predetermined confidence level based on the measured data. As a result, the regression analysis provides a statistically valid inference function between a dependent variable and an independent variable.

Figure 5:
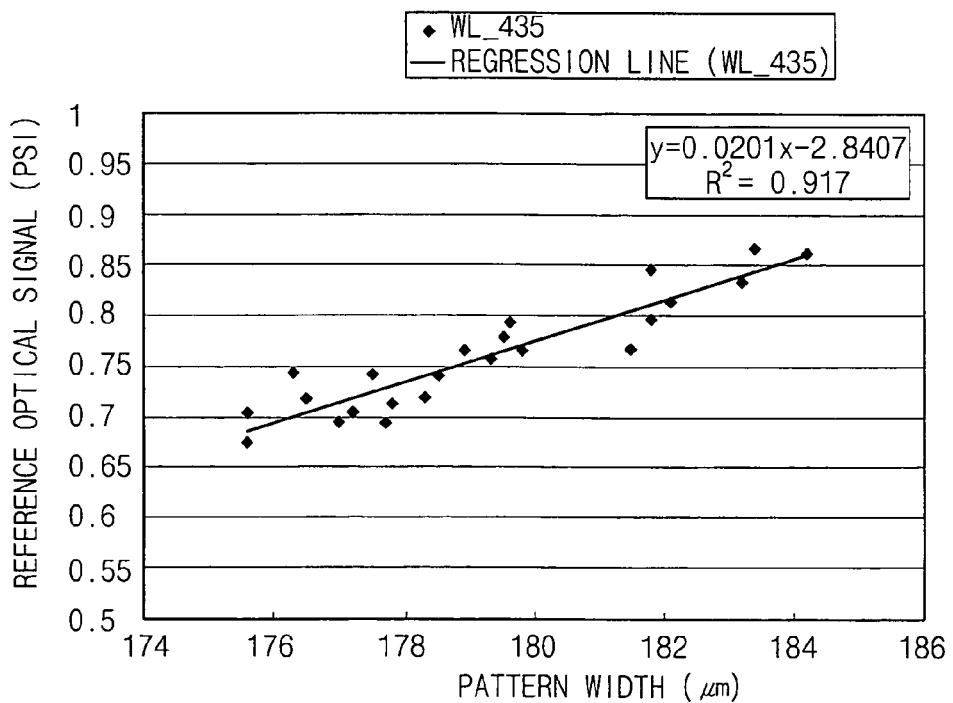
FIG. 5 is a graph of a regression line between the reference optical signal data and the measured pattern widths when the wavelength of the reference light is about 435 nm.

FIG. 5 is a graph of a regression line between the optical reference signal data and the measured pattern widths when the wavelength of the reference light is about 435 nm. In FIG. 5, a horizontal line indicates the measured pattern width, and a vertical line indicates the optical reference signal data. The regression analysis is conducted using a least squares method.

According to the least squares method used in this particular example, a first order function is selected as a mathematical model for the regression analysis, and an intercepting point and slope for the first function is inferred through an iterative statistical process, such that a summation of error squares is minimized. The error square indicates a square of the difference between an average of sampling data and the sampling data itself.

Supposing in one illustrative example that the mathematical model is expressed as the first order function of $Y_i = \alpha + \beta X_i$, an intercepting point $\alpha$ and a slope $\beta$ of the first function is statistically obtained as following equations:

$$\beta = \frac{S_{xy}}{S_{xx}}, \quad (2)$$
$$\alpha = \bar{y} - \beta \bar{x}$$

wherein, $$S_{xx} = \sum_{i=1}^{n} (x_i - \bar{x})^2, \quad (3)$$
$$S_{yy} = \sum_{i=1}^{n} (y_i - \bar{y})^2,$$
$$S_{xy} = \sum_{i=1}^{n} (x_i - \bar{x})(y_i - \bar{y})$$

In the above equation (2) and equation (3), x denotes the optical reference signal data, and $\bar{x}$ denotes an average of the optical reference signal data. In addition, y denotes the measured width of the photoresist pattern, and $\bar{y}$ denotes an average of the measured width of the photoresist pattern. The letter "n" denotes a number of sampling data, (e.g., 24 in the working example). The shape of the first order function indicates that y is an independent variable or a predictable variable and x is a dependent variable or a criterion variable. In other words, the optical reference signal data generated by the light irradiated onto the substrate of the inspection substrate is the dependent variable or the criterion variable, and the pattern characteristic data, such as the pattern width and/or the pattern thickness, is the independent variable or the predictable variable.

The optical reference signal data and the pattern characteristic data are statistically manipulated using equation (2) and equation (3) to thereby obtain an inferred regression line. The inferred regression line is expressed as the first order function shown in FIG. 5 with a coefficient of determination of about 0.917. The coefficient of determination numerically expresses a digression degree of each data from the regression line and is equal to a square of the correlation coefficient. Accordingly, the coefficient of determination is expressed as a real number in a range of zero to one, and the higher the coefficient of determination is, the higher the confidence level in the regression line.

In one embodiment, the coefficient of determination is set to be no less than about 0.6 in consideration of all the characteristics and processing conditions associated with the unit process of interest.

As a result, function generation unit 520 performs the regression analysis between the optical reference signal data in the reliable signal group having an allowable correlation coefficient and the reference pattern characteristic data to thereby generate a statistically valid inference function for the optical reference signal data and the reference pattern characteristic data with an allowable coefficient of determination.

With reference again to FIG. 1, operating member 500 further comprises an inference unit 530 adapted to calculate an inspection pattern characteristic data from the inference function and the inspection optical signal data, a determination unit 540 adapted to determine whether or not the inspection pattern characteristic data is within an allowable error tolerance range, and a buffer 510 adapted to temporarily store the optical reference signal data generated by detecting member 300. The inference function generated in function generation unit 520 and the inspection optical signal data stored in buffer 510 are transferred to inference unit 530, and the inspection pattern characteristic data is calculated from the optical reference signal data and the inference function in inference unit 530 to thereby generate an inferred inspection pattern characteristic data. Then, determination unit 540 determines whether the inferred inspection pattern characteristic data is included in the allowable error tolerance range. When the inferred inspection pattern characteristic data is out of the allowable error tolerance range, the inspection pattern is determined to be defective.

Although the foregoing examples discuss the correlation analysis and regression analysis between the reference optical signal data and the measured width of the photoresist pattern, the correlation analysis and the regression analysis could also be performed between the optical reference signal data and both the measured width and thickness of the photoresist pattern. In other words, a correlation analysis may be performed between the optical reference signal data and both the measured width and thickness of the pattern, and a statistical inference function formed using a multiple regression line.

The correlation degree between the optical reference signal data and both the measured width and thickness of the photoresist pattern is numerically expressed as a correlation coefficient vector, and the optical reference signal data functions as the criterion variable and the measured width and thickness of the photoresist pattern function as the predictable variable in the multiple regression line. As an exemplary embodiment, the coefficient of determination may be set to be not less than about 0.8 in the multiple regression analysis. The coefficient of determination may be variously set in view of various inspection conditions and processing conditions associated with the unit process of interest.

Apparatus 900 comprising stage 100, irradiating member 200, detecting member 300, storage member 400, and operating member 500 may in some embodiments be systematically controlled and connected through controller 600. In a related embodiment, a display member 700, comprising for example a computer monitor, may be further connected to controller 600 for visually displaying the results of determination unit 540.

With this arrangement, the results of determination unit 540 may be transferred to display member 700 by controller 600 so that pattern defects may be visually and directly verified on the display. When the inspection pattern is determined to have at least one defect via determination unit 540, controller 600 transfers the optical reference signal data from buffer 510 to first data file 410 in storage member 400. In addition, controller 600 also causes movement of inspection substrate W on support unit 110 of stage 100 to a position where the width of the photoresist pattern on the inspection substrate W may be actually measured. Controller 600 may transfer a driving signal to driver 130 and thus cause driving unit 120 to move support unit 110 to thereby adjust its position. Then, the inspection substrate W is transferred into an actual measurement chamber (not shown) by a transfer apparatus, such as a robot arm, and the width of the photoresist pattern is measured. The actual width of the inspection pattern is then stored into the second data file 420 of storage unit 400 by the controller 600.

As a result of the foregoing, as the inspection process is repeated over and over again, additional optical reference signal data and the pattern characteristic data are accumulated in storage unit 400 so that the confidence level of the inference function may be gradually improved since the inference function is statistically based on the optical reference signal data and the pattern characteristic data.

Even where the inspection pattern is determined to have no defects by determination unit 540, the actual width of the photoresist pattern and the corresponding optical reference signal data for the allowable pattern may be stored in storage unit 400 for future reference. However, the process of storing actual width measurements and corresponding optical reference signal data for allowable patterns is one directed to improving the confidence level of the inference function. Thus, the actual width and the corresponding optical reference signal data for an allowable pattern need not necessarily be stored in storage member 400 once the sample size for a particular statistical inference is sufficiently large so as to be sufficiently reliability.

Figure 6A:
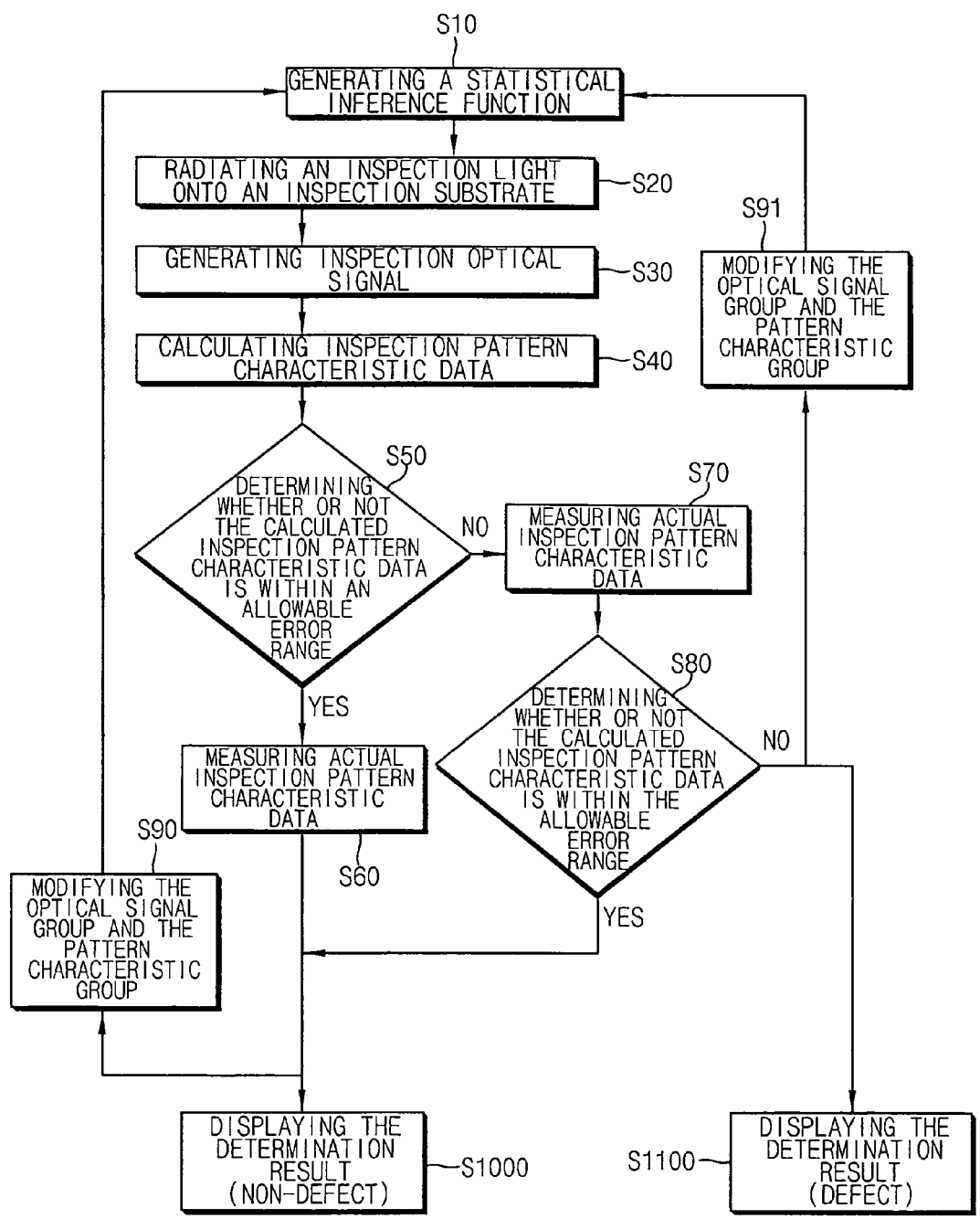
FIGS. 6A and 6B are flow charts illustrating a method of inspecting the inspection pattern according to an exemplary embodiment of the present invention.
Figure 6B:
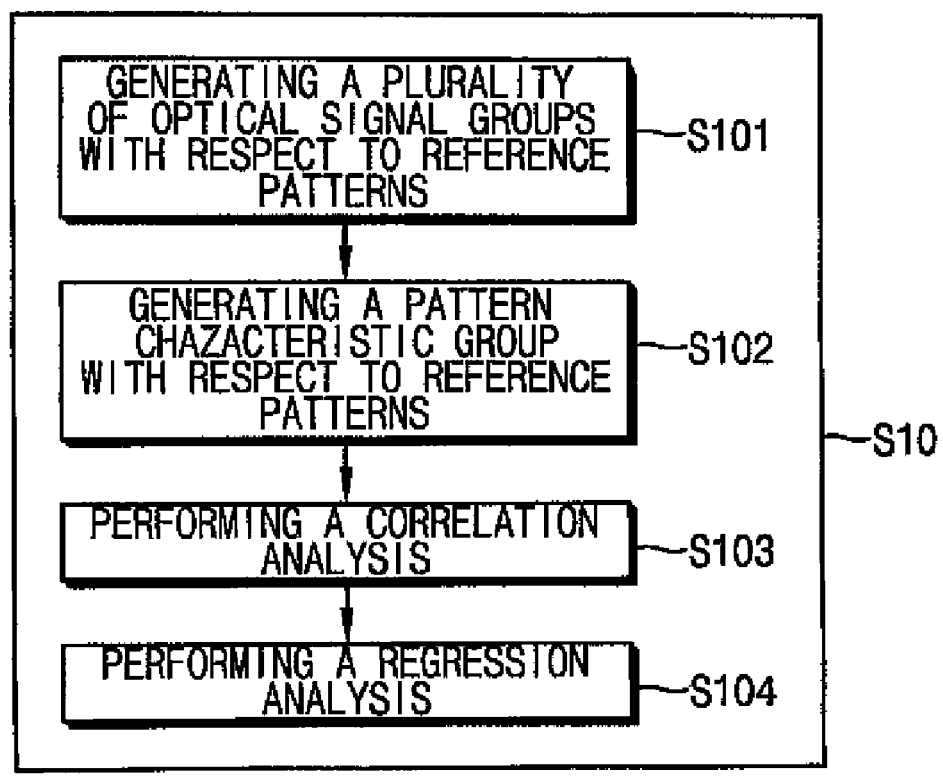

Hereinafter, an exemplary method of inspecting an inspection pattern will be described with reference to inspection apparatus 900 and with reference to FIGS. 1 to 5, 6A, and 6B. FIGS. 6A and 6B are a flow chart illustrating the exemplary method of inspecting the inspection pattern according to one embodiment of the invention.

Referring to FIGS. 6A and 6B, a statistical inference function is generated with respect to a reference pattern on a reference substrate for performing the above inspection method (S10).

As shown in FIG. 6B, a plurality of optical signal groups, each of which includes a plurality of optical reference signal data, is first formed in the larger process of generating the inference function (S101).

A plurality of reference substrates is prepared so as to generate reference data for the optical signal group, and the reference substrates undergo the same process as an inspection substrate. In other words, for a particular unit process of interest implicating an inspection pattern, reference substrates undergo the selected unit process under a variety of processing conditions normally in order to form reference patterns.

A light reflected from the reference pattern is detected and optical reference signal data is generated with respect to the reference pattern through a predetermined operation based on the reflected light. A measurement device or a spectroscope may be utilized to generate the optical reference signal data. In addition, a pattern characteristic, such as a thickness and a width of the reference pattern, is practically measured using a measurement device such as a SEM to thereby generate reference pattern characteristic data with respect to the reference pattern.

The optical reference signal data is classified into optical signal groups in accordance with the wavelength of a reference light used to irradiate the reference substrates, and the optical signal groups are stored in first data file 410 in storage unit 400. Accordingly, an optical signal group data stored in first data file 410 includes optical reference signal data generated by detecting reflected light having the same wavelength. In one particular embodiment, the optical reference signal data is measured non-destructively using a spectroscopic ellipsometer (SE). Polarized light is irradiated onto a surface of the reference substrate and detection lens 310 detects reflected polarized light. Then, the reflected polarized light is resolved into vertical and horizontal components in resolution unit 330. Data generation unit 320 calculates the intensity ratio ($\Psi$) and the phase difference ($\Delta$) between the vertical and horizontal components of the polarized reflection light based on a conventional SE theory. In one related embodiment, the tangent of the intensity ratio (tan $\Psi$) or the cosine of the phase difference (cos $\Delta$) are utilized as optical reference signal data. Alternatively, a laser irradiates the reference substrate with light at a selected wavelength and the intensity of the reflected light is stored as optical reference signal data. A conventional optical process for measuring pattern thickness may also be utilized to generate the optical reference signal data. As described above, the optical signal group includes a plurality of samplings for the optical reference signal data generated with reference light at the same wavelength, so that the optical signal group and the wavelength of the reference light have a one-to-one correspondence to each other.

In like manner as described above, a pattern characteristic group including a reference pattern characteristic data is generated and is stored in second data file 420 in storage unit 400 (S102).

A correlation analysis is conducted relating the optical reference signal data in each of the optical signal groups and the reference pattern characteristic data using correlation analyzer 522 (S103). An allowable correlation coefficient is selected from among the plurality of the correlation coefficients in function generation unit 520, and the optical signal group corresponding to the allowable correlation coefficient is selected as a reliable signal group. Then, a regression analysis is performed between the reference optical signal data in the reliable signal group and the reference pattern characteristic data in function generation unit 520 (S104). Accordingly, a statistically valid inference function is generated between the optical reference signal data and the reference pattern characteristic data.

For example, a linear regression analysis is performed between the optical reference signal data and the reference pattern characteristic data using a least squares method, so that a regression line is inferred as a first order function. The coefficient of determination for the regression line is selected in consideration of processing conditions related to the unit process of interest, related inspection pattern characteristics, process accuracy, etc. For example, when the inspection process is performed on the photoresist pattern, the coefficient of determination may usefully be selected to be not less than about 0.6.

Regression analysis in function generation unit 520 is performed only on the optical reference signal data in the reliable signal group, thus the confidence level associated with the regression analysis is improved.

Although the above exemplary embodiment discusses the correlation analysis and the regression analysis between the optical reference signal data and one kind of the reference pattern characteristic data, the correlation analysis and the regression analysis could also be performed between the optical reference signal data and at least two kinds of the reference pattern characteristic data, as would be well known to those skilled in the art. For example, a correlation analysis may be performed between the optical reference signal data and both of the width and thickness of the reference pattern and a statistically valid inference function may be formed using a multiple regression line. The correlation degree between the optical reference signal data and both the width and thickness of the reference pattern is numerically expressed as a correlation coefficient vector, and the reference optical signal data functions as the criterion variable and the width and thickness of the reference pattern function as the predictable variable in the multiple regression line. In one embodiment, the coefficient of determination may be set to be not less than about 0.8 in such a multiple regression analysis. The coefficient of determination may be variously set in view of various inspection conditions such as process characteristics of the unit process of interest and the process accuracy.

After generating the inference function with respect to the reference pattern, an inspection substrate W on which an inspection pattern is formed is secured on support unit 110 of stage 100, and the surface of the inspection substrate W is irradiated with an inspection light (S20). Then, a light reflected from inspection substrate W is detected by detection lens 310, and optical inspection signal data is generated by data generation unit 320.

The optical inspection signal data is generated (S30) in the same way as the optical reference signal data. In one embodiment, the optical inspection signal data may be derived non-destructively using a spectroscopic ellipsometer (SE). Polarized light at the reliable wavelength is irradiated onto a surface of the inspection substrate W, and detection lens 310 detects reflected polarized light. Then, the reflected polarized light is resolved into vertical and horizontal components in resolution unit 330. Data generation unit 320 calculates the intensity ratio ($\Psi$) and the phase difference ($\Delta$) between the vertical and horizontal components of the polarized reflection light using conventional SE theory. In such a case, the tangent of the intensity ratio (tan $\Psi$) or the cosine of the phase difference (cos $\Delta$) may be utilized as the optical inspection signal data. Thus, in one embodiment, the tangent of the intensity ratio (tan $\Psi$) is selected as the optical inspection signal data and is stored in buffer 510 of operating member 500.

Then, the inference function generated in function generation unit 520 and the optical inspection signal data stored in buffer 510 are transferred to inference unit 530. In inference unit 530, inspection pattern characteristic data is calculated from the inference function and the optical inspection signal data (S40). When the inference function is a first order function between the optical reference signal data and measured widths of a photoresist pattern as described above, the inspection pattern characteristic data is inferentially obtained as corresponding to the optical inspection signal data based on the inference function. Then, determination unit 540 determines whether or not the calculated inspection pattern characteristic data is within an allowable error tolerance range (S50). When the calculated inspection pattern characteristic data is outside the allowable error tolerance range, the inspection pattern is determined to have a defect, and the pattern characteristic of the inspection pattern is actually measured using a measurement device such as a SEM (S70). The above inspection results relating to the defect are shown on the display unit 700 (S1100). When the calculated inspection pattern characteristic data is within the allowable error tolerance range, the inspection pattern is determined to have no defect. The above inspection results of the non-defect are also shown on display unit 700 (S1000).

Controller 600 stores the optical inspection signal data into the first data file 410 of storage unit 400, and also stores the actual inspection pattern characteristic data in the second data file 420 of the storage unit 400, so that the current optical inspection signal data is added to the stored body of optical reference signal data and the actual inspection pattern characteristic data is also added to the reference pattern characteristic data. Accordingly, the statistical sample size for the optical signal group and the pattern characteristic group is increased (S90). Regression analysis operations are subsequently performed in relation to the expanded signal group and the pattern characteristic group, so that, potentially a modified inference function is generated. Thereafter, the inspection pattern characteristic data is calculated from the modified inference function and the optical inspection signal data, so that the confidence level for the regression analysis is gradually improved as the sample size of the optical signal group and the pattern characteristic group is increased.

When the calculated inspection pattern characteristic data is within the allowable error tolerance range, the inspection pattern is determined to have no defect, and the above inspection results of the non-defect are shown on display unit 700 (S1000), thereby completing the inspection process.

Although the inspection pattern is determined to have no defect by determination unit 540, controller 600 may transfer the inspection optical signal data stored in buffer 510 to the first data file 410 of storage unit 400, and also transfer actual pattern characteristic data measured with respect to the inspection substrate W to the second data file 420 of storage unit 400. Accordingly, the current optical inspection signal data is added to the body of optical reference signal data and the actual inspection pattern characteristic data may be added to the reference pattern characteristic data even in a case where the inspection pattern is determined to have no defects in order to increase the optical signal group and the pattern characteristic group (S90).

Using the dictates taught by the foregoing embodiments, the rate inspection processes may be remarkably improved as compared with a conventional inspection processes. In addition, the inspection process provided by the present invention requires no physical measurement, and thus various kinds of the inspection pattern may be inspected without an additional treatment, or potentially destructive physics intrusion.

According to various embodiments of the invention, the inspection pattern characteristic data may be calculated from a statistical inference function and optical inspection signal data in order to determine whether or not the pattern falls within an allowable error tolerance range. In this manner, the cost and time associated with inspection processes are remarkably reduced. In addition, the optical inspection signal data and the inspection pattern characteristic data that are actually measured in the inspection process may be accumulated into an established optical signal group and pattern characteristic group, so that the confidence level of the inference function may be gradually improved as the inspection process is repeated. As a result, although inspection of a particular pattern characteristic is not actually performed, pattern defects may be accurately detected using the inference function. Furthermore, since the optical inspection signal data is accumulated and repeatedly utilized during each inspection process, an expensive apparatus for analyzing the optical signal data is no longer needed. The inspection efficiency is remarkably improved since the inspection process mainly depends on a statistical treatment operated in a computer system, so that a throughput of the inspection process is remarkably increased.

Although the exemplary embodiments of the present invention have been described, it is understood that the present invention should not be limited to only these exemplary embodiments. On the contrary, various changes and modifications may be made to the foregoing as will be understood by one of ordinary skill in the art and as such these modifications and alterations will fall within the scope of the present invention as hereinafter claimed.

What is claimed is:

1. A method of inspecting an inspection pattern formed on an inspection substrate by a unit process, comprising:
generating a statistical inference function corresponding to optical reference signal data and reference pattern characteristic data associated with a plurality of reference patterns formed on reference substrates by the unit process;
obtaining optical inspection signal data from inspection light reflected from the inspection pattern;
calculating inspection pattern characteristic data from the optical inspection signal data and the statistical inference function; and
determining whether or not the calculated inspection pattern characteristic data falls within an allowable error tolerance range,
wherein generating the statistical inference function comprises forming first and second optical signal groups, the first optical signal group comprises optical reference signal data generated when reference light having a first wavelength is irradiated onto the reference patterns, and the second optical signal group comprises optical reference signal data generated when reference light having a second wavelength different than the first wavelength is irradiated onto the reference patterns.

2. The method of claim 1, wherein generating the statistical inference function further comprises:
forming a pattern characteristic group comprising reference pattern characteristic data;
repeatedly performing a correlation analysis between the optical reference signal data in each optical signal group and reference pattern characteristic data to thereby obtain a correlation factor corresponding to each of the optical signal groups; and
performing a regression analysis between optical reference signal data in a reliable signal group and reference pattern characteristic data to thereby generate a regression line associated with the statistical inference function, wherein the reliable signal group is one of the optical signal groups, corresponds to an allowable correlation factor, and corresponds to a reliable wavelength for the inspection light.

3. The method of claim 2, wherein the inspection light comprises light having ultraviolet or deep ultraviolet wavelengths; and
wherein the optical inspection signal data comprises an intensity value associated with the reflected inspection light.

4. The method of claim 2, wherein the inspection light comprises polarized light, and wherein the optical inspection signal data corresponds to a tangent of a ratio between a vertical component and a horizontal component of the polarized light, or a cosine of a phase difference between the vertical component and the horizontal component of the polarized light.

5. The method of claim 2, wherein the correlation factor includes a Pearson's correlation coefficient.

6. The method of claim 5, wherein the allowable correlation factor includes an absolute value of the Pearson's correlation coefficient not less than about 0.9.

7. The method of claim 2, wherein the reference pattern characteristic data is derived from measurements made with a scanning electron microscope (SEM).

8. The method of claim 2, wherein the reference pattern characteristic data corresponds to the width or thickness of a reference pattern and wherein the regression line comprises a simple regression line using the width or thickness of the reference pattern as a predictor and the optical inspection signal data as a criterion.

9. The method of claim 8, wherein a simple determination coefficient for the simple regression line is in a range from not less than about 0.6, the simple determination coefficient being determined in accordance with characteristics associated with the unit process.

10. The method of claim 2, wherein the reference pattern characteristic data comprises the width and thickness of the reference pattern, and the regression line comprises a multiple regression line using the width and thickness of the reference pattern as a predictor and the optical inspection signal data as a criterion.

11. The method of claim 10, wherein a multiple determination coefficient for the multiple regression line is in a range from not less than about 0.8, the multiple determination coefficient being determined in accordance with characteristics associated with the unit process.

12. The method of claim 1, wherein the reference pattern and the inspection pattern comprise a photoresist pattern.

13. The method of claim 1, further comprising:
deriving actual inspection pattern characteristic data by physically measuring the pattern characteristic where calculated inspection pattern characteristic data falls out of the allowable error tolerance range.

14. The method of claim 13, wherein the physical measuring comprises scanning the pattern characteristic with a scanning electron microscope (SEM).

15. The method of claim 14, further comprising:
adding current optical inspection signal data to the reference pattern optical signal data in relation to the wavelength of the inspection light to thereby modify the corresponding optical signal group;
adding the actual inspection pattern characteristic data to the reference pattern characteristic data to thereby modify the corresponding pattern characteristic group; and thereafter,
generating a modified statistical inference function from the modified optical signal group and the modified pattern characteristic group.

16. The method of claim 1, further comprising:
deriving actual inspection pattern characteristic data to thereby form a plurality of actual inspection pattern characteristic data;
adding current optical inspection signal data to the reference pattern optical signal data in relation to the wavelength of the inspection light to thereby modify the optical signal group;
adding the actual inspection pattern characteristic data to the reference pattern characteristic data to thereby modify the pattern characteristic group; and
generating a modified statistical inference function in relation to the modified optical signal group and the modified pattern characteristic group.

17. An apparatus for inspecting an inspection pattern formed on an inspection substrate by a unit process, comprising:
a stage adapted to secure the inspection substrate;
an irradiating member adapted to irradiate the inspection substrate with inspection light;
a detecting member adapted to detect inspection light reflected from the inspection substrate and generate optical inspection signal data corresponding to the reflected inspection light; and
an operating member adapted to determine whether a pattern defect is present in the inspection pattern by calculating inspection pattern characteristic data using a statistical inference function, wherein the statistical inference function corresponds to a relationship between optical reference signal data of a reliable optical signal group and reference pattern characteristic data,
wherein the operating member comprises a correlation analyzer measuring for each of a plurality of optical signal groups a correlation factor between optical reference signal data of the optical signal group and the reference pattern characteristic data,
wherein reference light of different wavelengths is used to obtain the optical reference signal data of different optical signal groups, respectively, and
wherein the plurality of optical signal groups comprises the reliable optical signal group.

18. The apparatus of claim 17, wherein the reference pattern characteristic data is derived from a plurality of reference patterns formed on reference substrates by the unit process.

19. The apparatus of claim 18, wherein the stage comprises a support unit adapted to support the inspection substrate and a drive unit adapted to move the support unit.

20. The apparatus of claim 18, wherein the irradiating member comprises:
a light source adapted to generating the inspection light; and
a beam splitter adapted to transforming the inspection light into a slit light, and
wherein the detecting member comprises:
a detection lens adapted to detect the reflected inspection light; and,
a data generation unit adapted to generate the optical inspection signal data from the reflected inspection light.

21. The apparatus of claim 20, wherein the light source comprises a krypton fluoride (KrF) excimer laser, an argon fluoride (ArF) excimer laser, a fluorine (F2) excimer laser or an argon (Ar) excimer laser.

22. The apparatus of claim 20, wherein the inspection light comprises light having an ultraviolet or deep ultraviolet (DUV) wavelength; and,
wherein the data generation unit comprises a charge coupled device (CCD) adapted to detect intensity of the reflected inspection light, such that the optical inspection signal data corresponds to the detected intensity of the reflected inspection light.

23. The apparatus of claim 18, wherein the irradiating member comprises:
a light source adapted to generate the inspection light and a polarizer for transforming the inspection light into a polarized light; and,
wherein the detecting member comprises:
a detection lens adapted to detect polarized light reflected from the inspection substrate;
a resolution unit adapted to resolve the reflected polarized light into vertical and horizontal components; and,
a data generation unit adapted to generate the optical inspection signal data from the vertical and horizontal components.

24. The apparatus of claim 23, wherein the data generation unit calculates an intensity ratio ($\Psi$) between the vertical and horizontal components of the reflected polarized light, and the optical inspection signal data corresponds to a tangent of the intensity ratio ($\tan \Psi$).

25. The apparatus of claim 23, wherein the data generation unit calculates a phase difference ($\Delta$) between the vertical and horizontal components of the reflected polarized light, and the optical inspection signal data corresponds to a cosine of the phase difference ($\cos \Delta$).

26. The apparatus of claim 18, wherein the operating member further comprises:
- a buffer adapted to temporarily store the optical inspection signal data;
- a function generation unit adapted to generate the statistical inference function from the optical reference signal data of the reliable optical signal group and the reference pattern characteristic data;
- an inference unit adapted to calculate the inspection characteristic data using the statistical inference function and the optical inspection signal data; and,
- a determination unit adapted to determining whether or not the calculated inspection characteristic data falls within an allowable error tolerance range.

27. The apparatus of claim 26, further comprising:
- a storage member storing the plurality of optical signal groups in a first data file; and,
- storing a pattern characteristic group in a second data file;
- wherein each optical signal group comprises optical reference signal data and the pattern characteristic group comprises reference pattern characteristic data; and
- wherein different wavelengths of reference light is supplied onto the reference substrates to obtain the optical reference signal data of different optical signal groups.

28. The apparatus of claim 27, wherein the function generation unit comprises:
- a regression analyzer adapted to perform a regression analysis between the optical reference signal data of one of the optical signal groups and the reference pattern characteristic data transmitted to the function generation unit from the first and second data files, respectively.

29. The apparatus of claim 28, wherein:
- the correlation factor corresponding to the reliable optical signal group is an allowable correlation factor; and,
- the regression analyzer performs the regression analysis between the optical reference signal data in the reliable signal group and the reference pattern characteristic data.

30. The apparatus of claim 28, further comprising:
- a controller adapted to store the optical inspection signal data to the first data file and at least one actual inspection pattern characteristic datum to the second data file where the calculated inspection pattern characteristic data is out of the allowable error tolerance range.

31. The apparatus of claim 18, wherein the inspection pattern characteristic data and the reference pattern characteristic data include width or thickness of the inspection pattern and the reference pattern, respectively.

32. The apparatus of claim 31, wherein the statistical inference function includes a simple regression line of which a predictable variable is the width or thickness of the inspection pattern and of which a criterion variable is the optical inspection signal data.

33. The apparatus of claim 18, wherein the inspection pattern characteristic data and the reference pattern characteristic data include width and thickness of the inspection pattern and the reference pattern, respectively.

34. The apparatus of claim 33, wherein the statistical inference function includes a multiple regression line of which a predictable variable is the width and thickness of the inspection pattern and of which a criterion variable is the optical inspection signal data.

35. The apparatus of claim 18, further comprising a display member adapted to display information regarding whether or not the inspection pattern has a defect.

* * * * *